United States Patent
Evans et al.

(10) Patent No.: US 10,217,598 B2
(45) Date of Patent: Feb. 26, 2019

(54) X-RAY GENERATOR

(71) Applicant: ADAPTIX LTD., Oxfordshire (GB)

(72) Inventors: Mark Evans, Oxon (GB); Robert Stevens, Wiltshire (GB); Gil Travish, Oxford (GB)

(73) Assignee: ADAPTIX LIMITED, Oxfordshire (GB)

( * ) Notice: Subject to any disclaimer, the term of this patent is extended or adjusted under 35 U.S.C. 154(b) by 219 days.

(21) Appl. No.: 15/121,437

(22) PCT Filed: Mar. 5, 2015

(86) PCT No.: PCT/GB2015/050639
§ 371 (c)(1),
(2) Date: Aug. 25, 2016

(87) PCT Pub. No.: WO2015/132595
PCT Pub. Date: Sep. 11, 2015

(65) Prior Publication Data
US 2016/0372298 A1    Dec. 22, 2016

(30) Foreign Application Priority Data

Mar. 5, 2014    (GB) .................................. 1403901.0

(51) Int. Cl.
| | | |
|---|---|---|
| *H01J 35/30* | (2006.01) | |
| *H01J 35/06* | (2006.01) | |
| *A61B 6/00* | (2006.01) | |

(52) U.S. Cl.
CPC ............ *H01J 35/30* (2013.01); *H01J 35/065* (2013.01); *A61B 6/4007* (2013.01); *H01J 2235/068* (2013.01); *H01J 2235/087* (2013.01)

(58) Field of Classification Search
None
See application file for complete search history.

(56) References Cited

U.S. PATENT DOCUMENTS

| | | |
|---|---|---|
| 6,241,651 B1 | 6/2001 | Smith et al. |
| 7,218,700 B2 | 5/2007 | Huber et al. |
| | (Continued) | |

FOREIGN PATENT DOCUMENTS

| | | |
|---|---|---|
| JP | S60256036 A | 12/1985 |
| WO | 2011/017645 A2 | 10/2011 |

OTHER PUBLICATIONS

C. Ribbing, "Microfabrication of miniature x-ray source and x-ray refractive lens," Comprehensive Summaries of Uppsala Dissertations from the Faculty of Science and Technology 787, 2002.

(Continued)

*Primary Examiner* — Hoon K Song
(74) *Attorney, Agent, or Firm* — Reichel Stohry LLP; Mark C. Reichel; Natalie J. Dean

(57) ABSTRACT

An x-ray generator may include a plurality of electron field emitters; a target material; a plurality of energizable solenoid coils; and an electronic power and timing circuit. The generator may provide electrical current to at least one individual solenoid coil to create a magnetic field to cause the path of electrons emitted from the emitter closest to the energized solenoid coil to be defocused and/or deflected before the electrons reach the target material. The target material may comprise a low atomic number material and a high atomic number material, the high atomic number material being arranged in a regular pattern, such that, in use, the electrons may be aimed at either the high or the low atomic number material.

23 Claims, 5 Drawing Sheets

(56) References Cited

U.S. PATENT DOCUMENTS

| | | | |
|---|---|---|---|
| 2008/0084967 A1 | 4/2008 | Matsuo et al. | |
| 2010/0172475 A1* | 7/2010 | Behling | H01J 35/10 378/137 |
| 2011/0075802 A1 | 3/2011 | Beckmann et al. | |
| 2011/0122922 A1 | 5/2011 | Hanke et al. | |
| 2011/0188634 A1* | 8/2011 | Lee | H01J 1/304 378/122 |

OTHER PUBLICATIONS

Search Report for International Patent Application No. GB1403901.0, dated Aug. 20, 2014.
Examination Report under Section 18(3), Application No. GB1403901.0, dated Mar. 30, 2017.

* cited by examiner

X-RAY GENERATOR

CROSS-REFERENCE TO RELATED APPLICATIONS

This application claims the benefit of International Application No. PCT/GB2015/050639 filed on Mar. 5, 2015, and published as WO 2015/132595 A1, and International Patent Application No. GB 1403901.0 filed on Mar. 5, 2014, which are hereby incorporated by reference in their entirety.

FIELD OF INVENTION

The present invention(s) relate generally to an x-ray generator and a method of obtaining an x-ray image of an object and finds particular, although not exclusive, utility in an x-ray generator comprising a plurality of x-ray sources.

BACKGROUND

In recent years there have been advances in the development of micrometer scale x-ray sources, such that it is now possible to produce a plurality of x-ray sources with a typical distance between the x-ray sources of the order of 100 μm to 1 cm or more.

An example of such a two-dimensional x-ray source is provided in WO 2011/017645 "apparatus for producing x-rays for use in imaging".

Known two-dimensional x-ray sources as in WO 2011/017645 have all of their sources on simultaneously, i.e. at the point of initiating the x-ray emission field emission the surface electrons will occur at each of the field emitters and x-ray photons (bremsstrahlung) will be emitted simultaneously from multiple sites as electrons strike the target material.

For certain x-ray imaging modalities it may be desirable to be able to control the sequence of the activation of individual x-ray sources within a plurality of x-ray sources. For example, it may be advantageous to activate the x-ray sources in a sequential and row by row manner known as raster scanning which is used in many electronic imaging devices.

A well known problem in electron and x-ray generation is the control of the electron current and hence of the resulting x-ray flux. In conventional systems, intermediate voltage grids are sometimes used to blank the electron emission. In other cases, high voltage switches are used to shut off the potential. In still other configurations, such as those found in Spindt arrays, transistors control the moderate-voltage supplied to each of the field-enhanced emitters and a further stage is used to increase the voltage (energy) of the electrons to the final end-point energy desired from the x-ray source.

Extending these methods to large arrays can prove impractical and costly. Grids can limit the emitter density and introduce a source of arcing and breakdown. Transistor arrays can lead to complex switching controls and the low voltages of emission can lead to reduced current due to space charge effects. Therefore, it is desirable to invent a new mechanism of controlling the production of x-rays from arrays of electron emitters; one which does not rely on high voltage switching.

SUMMARY OF THE DISCLOSURE

It is an aim of embodiments of the present invention(s) to provide a means of selectively controlling the x-ray emission whereby multiple x-ray sources can be individually activated, via a mechanism which does not rely on high voltage switching. It is a further aim of embodiments of the present invention(s) to provide a means of controlling the sequence of activation of a plurality of x-ray sources whereby the resulting activation sequence, such as but not limited to raster scanning, can be synchronised with the emitter electrons and plurality of detecting elements where each detecting element is individually controlled according to the diagnostic requirements of the x-ray imaging application.

In a first aspect, an embodiment of the invention may provide an x-ray generator, comprising a plurality of electron field emitters; a target material arranged to emit x-ray photons when electrons are incident upon it; a plurality of energisable solenoid coils positioned adjacent to the plurality of electron field emitters; and an electronic power and timing circuit configured to provide electrical current to at least one individual solenoid coil; wherein, at least one individual solenoid coil is configurable such that when energised, a magnetic field is created causing the path of electrons emitted from the emitter closest to the at least one individual energised solenoid coil to be defocused and/or deflected before the electrons reach the target material; and wherein the target material comprises a low atomic number material and a high atomic number material, the high atomic number material being arranged in a regular pattern, such that, in use, the electrons emitted by the emitter, impinge upon either the high atomic number material when they are deflected and/or defocussed by the energised individual solenoid coil, and upon the low atomic number material when they are not deflected and/or defocussed by the individual solenoid coil closest to the emitter, or impinge upon the low atomic number material when they are deflected and/or defocussed by the energised individual solenoid coil, and upon the high atomic number material when they are not deflected and/or defocussed by the individual solenoid coil closest to the emitter.

In a second aspect, an embodiment of the invention may provide a method of obtaining an x-ray image of an object, comprising the steps of providing an x-ray generator according to the first aspect; providing an x-ray detector; and operating said generator whereby x-ray photons pass through an object positioned between the x-ray source array and the x-ray detector.

The above and other characteristics, features and advantages of embodiments of the present invention(s) will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

DETAILED DESCRIPTION

Figure 1:
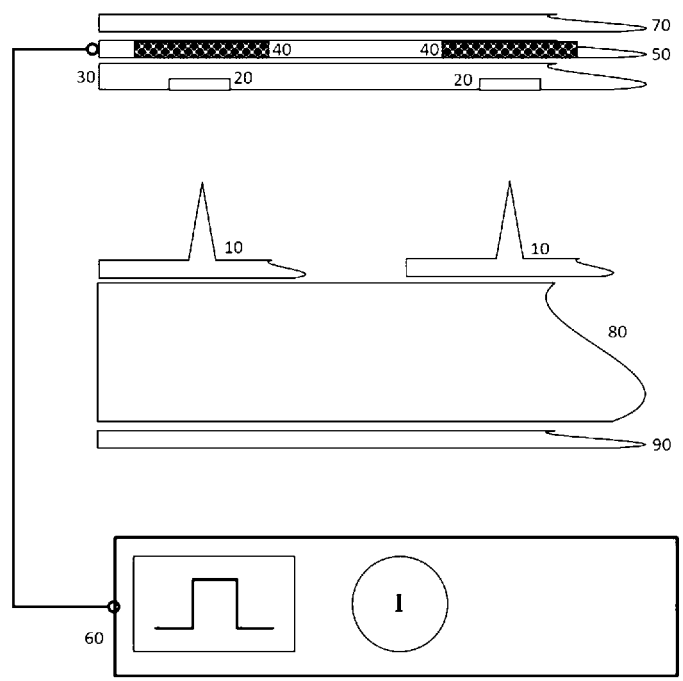
FIG. 1 is a schematic representation of an x-ray generator.

Embodiments of the present invention(s) will be described with respect to certain drawings but the invention(s) are not limited thereto but only by the claims. The drawings described are only schematic and are non-limiting. Each drawing may not include all of the features of the invention and therefore should not necessarily be considered to be an embodiment of the invention. In the drawings, the size of some of the elements may be exaggerated and not drawn to scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that operation is capable in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that operation is capable in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the claimed invention(s), the only relevant components of the device are A and B.

Similarly, it is to be noticed that the term "connected", used in the description, should not be interpreted as being restricted to direct connections only. Thus, the scope of the expression "a device A connected to a device B" should not be limited to devices or systems wherein an output of device A is directly connected to an input of device B. It means that there exists a path between an output of A and an input of B which may be a path including other devices or means. "Connected" may mean that two or more elements are either in direct physical or electrical contact, or that two or more elements are not in direct contact with each other but yet still co-operate or interact with each other. For instance, wireless connectivity is contemplated.

Reference throughout this specification to "an embodiment" or "an aspect" means that a particular feature, structure or characteristic described in connection with the embodiment or aspect is included in at least one embodiment or aspect of the present invention(s). Thus, appearances of the phrases "in one embodiment", "in an embodiment", or "in an aspect" in various places throughout this specification are not necessarily all referring to the same embodiment or aspect, but may refer to different embodiments or aspects. Furthermore, the particular features, structures or characteristics of any embodiment or aspect of the invention may be combined in any suitable manner, as would be apparent to one of ordinary skill in the art from this disclosure, in one or more embodiments or aspects.

Similarly, it should be appreciated that in the description various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Moreover, the description of any individual drawing or aspect should not necessarily be considered to be an embodiment of the invention. Rather, as the following claims reflect, inventive aspects lie in fewer than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some features included in other embodiments, combinations of features of different embodiments are meant to be within the scope of the invention, and form yet further embodiments, as will be understood by those skilled in the art. For example, in the following claims, any of the claimed embodiments can be used in any combination.

In the description provided herein, numerous specific details are set forth. However, it is understood that embodiments of the invention may be practised without these specific details. In other instances, well-known methods, structures and techniques have not been shown in detail in order not to obscure an understanding of this description.

In the discussion of the invention(s), unless stated to the contrary, the disclosure of alternative values for the upper or lower limit of the permitted range of a parameter, coupled with an indication that one of said values is more highly preferred than the other, is to be construed as an implied statement that each intermediate value of said parameter, lying between the more preferred and the less preferred of said alternatives, is itself preferred to said less preferred value and also to each value lying between said less preferred value and said intermediate value.

The use of the term "at least one" may mean only one in certain circumstances.

The principles of the invention(s) will now be described by a detailed description of at least one drawing relating to exemplary features of one or more embodiments of the invention(s). It is clear that other arrangements can be configured according to the knowledge of persons skilled in the art without departing from the underlying concept or technical teaching of the invention(s), the invention(s) being limited only by the terms of the appended claims.

In FIG. 1 a schematic representation of the components used in one embodiment of the x-ray generator is shown.

Electrons are emitted from the electron emitter source 10. The electron emitter may be formed by a lithium niobate pyroelectric crystal 80 with an upper surface and a conducting film coating the upper surface of the pyroelectric crystal.

The pyroelectric crystal includes a plurality of field emitters formed as micrometer-scale exposed regions in the pyroelectric crystal having one or more sharp peaks or ridges. The pyroelectric crystal is alternately heated and cooled over a period of several minutes with a heater/cooler 90 adjacent the pyroelectric crystal so that spontaneous charge polarisation occurs in the pyroelectric crystal. The spontaneous charge polarisation causes a perpendicular electric field to arise on the pyroelectric crystal's top and bottom faces, in which case at the exposed surface of the pyroelectric crystal the electric field is enhanced by the sharp peaks or ridges, thereby causing field emission of surface electrons from that location. X-rays are produced when the emitted electrons strike a target material located adjacent to the emitting face.

The electrons travel towards a target material comprising a plurality of tungsten targets 20 contained within a silicon substrate 30. Adjacent to the tungsten targets 20 is a plurality of solenoid coils 50 with each individual solenoid coil 40 supplied current from a power supply 60. The power supply 60 being configured such that in use adjacent solenoid coils are energised within 1 ms to 5 ms of each other.

Figure 2:
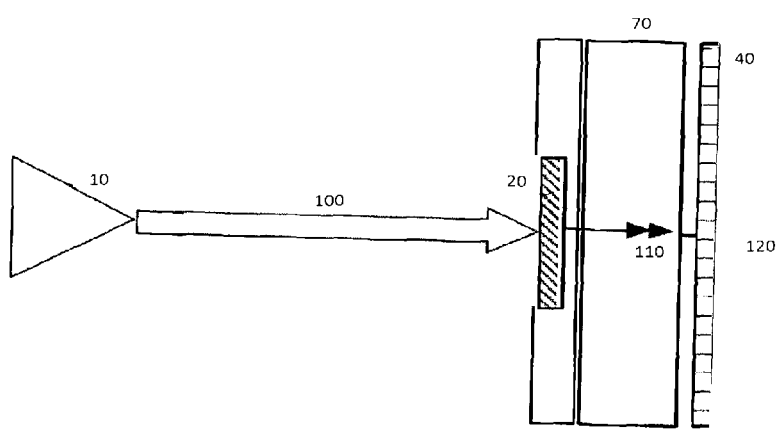
FIG. 2 is a schematic representation of the flow of electrons and x-ray photons where the solenoid coils are in axial alignment with the field emitters and the target area and the solenoid is powered off and electrons emitted from the source are focused upon the target material.

A schematic representation in FIG. 2 shows the flow of electrons 100 and x-ray photons 110 when the solenoid coils 40 are in axial alignment with the emitters 10 and the solenoid coils 40 are powered off and electrons from the emitter source 10 impinge on the tungsten target 20.

In this embodiment the aluminium filter material 70 is positioned between the target 20 and the solenoid 40, however the principle of operation is the same as when the aluminium filter material 40 is positioned behind the solenoid 40 as shown in FIG. 1.

The x-ray photons 110 produced when the electrons 100 impinge upon the target material 20 pass through the aluminium filter material 70 which absorbs the low energy (or soft) x-ray photons such that the x-ray photons emerging past the solenoid 40 are just high energy (or hard) x-ray photons 120.

Figure 3:
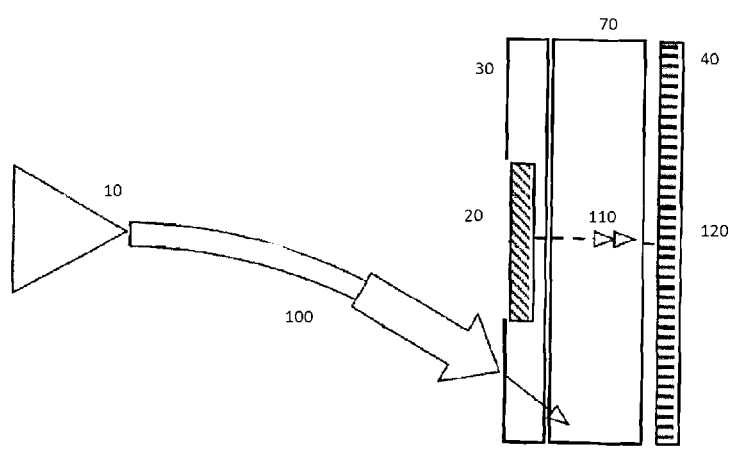
FIG. 3 is a schematic representation of the flow of electrons and x-ray photons where the solenoid coils are in axial alignment with the field emitters and the target area and the solenoid is powered on and electrons emitted from the source are deflected away from the target material.

A schematic representation in FIG. 3 shows the flow of electrons 100 and x-ray photons 110 where the solenoid coils 40 are in axial alignment with the emitters 10 and the solenoid coils 40 are powered on and electrons 100 emitted from the source 10 are deflected away from the high-Z target material 20, towards the low-Z material 30.

This operates in essentially the same manner as in FIG. 2 except that in this case power is supplied to the solenoid coil 40. In the "on" state the solenoid coil deflects the electrons 100 away from the target material 20. Thus the x-ray photons produced 110 are relatively few and low energy (or soft) x-ray photons which are mainly absorbed in the filter material 70 resulting in relatively few (less than 1% of the x-ray photons compared to the "off" state) passing through the solenoid 40 and being available for a subsequent x-ray imaging process 120.

Figure 4:
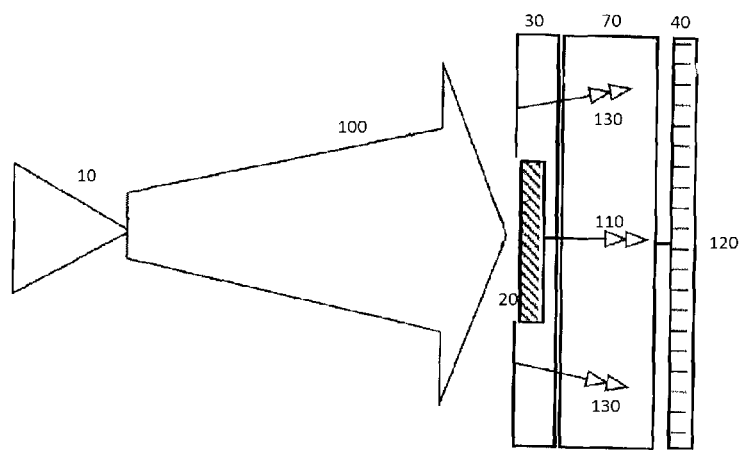
FIG. 4 is a schematic representation of the flow of electrons and x-ray photons where the solenoid coils are not in axial alignment with the field emitters and the target area and the solenoid is powered on and electrons emitted from the source are defocused towards the target material.

A schematic representation in FIG. 4 shows the flow of electrons 100 and x-ray photons 110 where the solenoid coils 40 are not in axial alignment with the field emitters 10 and the solenoid coils 40 are powered on and electrons 100 emitted from the emitters 10 are defocused away from the target material 20 contained within the substrate 30.

Here the solenoid 40 defocuses the electron beam 100 away from the target material 20 and resulting in relatively few hard x-ray photons 110 compared with a greater number of soft (low energy) x-ray photons 130 which are absorbed by the aluminium filter material 70. The x-ray photons 110 emerging from the x-ray filter material 70 pass through the solenoid 40 and being available for a subsequent x-ray imaging process 120.

Figure 5:
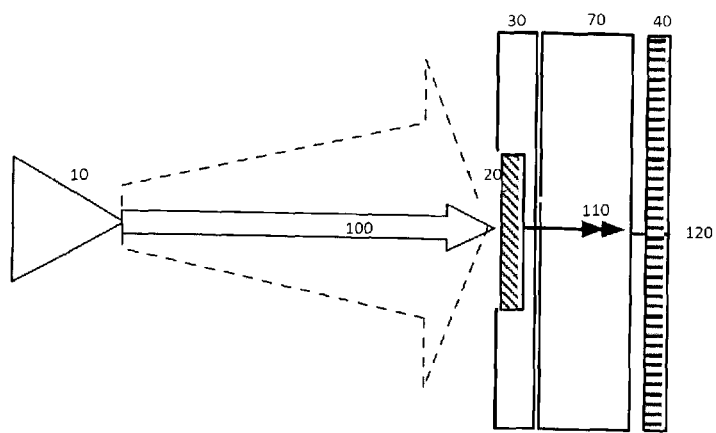
FIG. 5 is a schematic representation of the flow of electrons and x-ray photons where the solenoid coils are not in axial alignment with the field emitters and the target area and the solenoid is powered off and electrons emitted from the source are focused towards the target material.

A schematic representation in FIG. 5 shows the flow of electrons 100 and x-ray photons 110 where the solenoid coils 40 are not in axial alignment with the field emitters 10 and the solenoid coils 40 are powered off and electrons 100 emitted from the emitter source 10 are focused towards the target material 20.

Here the solenoid coils 40 focus the electron beam 100 towards the target material 20 resulting in a larger number of hard x-ray photons 110 which pass through the aluminium filter material 70 and emerge 120 on the other side of the solenoid 40.

As used herein, the term "adjacent" may include wherein at least some of the plurality of coils are arranged to surround the emitter. Further, the term "adjacent" may mean that the coils are arranged behind the target material relative to the electron field emitters and/or are behind the electron field emitters relative to the target material. In other words, the coils may not be located in, or adjacent to, the path of the electrons from the emitters to the target material. The coils may be said not to be located between the emitters and target material.

Whether the electrons are defocused or deflected is determined by the alignment of the solenoid coils relative to the alignment of the field emitters which act as the source of the electrons which when accelerated by the application of an applied voltage strike at the target material causing the emission of x-rays.

If the solenoid coils are in axial alignment with the field emitters and the target area, then a current applied through the solenoid coils will cause the electrons to be focused. If the solenoid coils are spatially arranged to be laterally offset between the direct alignment of the electron field emitters and the target area, then a current applied through the solenoid coils will cause the electrons to be defocused and deflected.

It has been found that offsetting the solenoid coils relative to the electron field emitters reduces the current density required through the solenoid coils in order to cause a given percentage of electrons to deviate sufficiently from the course they would take with no current applied through the solenoid coils. For this reason, it is desirable for the solenoid coils to be offset from the electron field emitters, although positioning the solenoid coils in alignment with the electron field emitters causes the invention to operate in the same fundamental manner but requiring a higher solenoid current. The offset may be in the range of 1-3 mm although other offset dimensions are possible.

Here it can be understood that defocusing can mean the increase in either the area or the diameter of the electron distribution's transverse profile under the influence of an energised coil. The specific magnetic-optics ratio of offset to defocusing that is optimal is dependent on the target size, distance to the target (cathode-anode spacing), and the emitter pitch, among other factors. This magnetic-optics ratio may lie in the range 1000:1 to 1:1. In practice, the coil and target parameters are adjusted until there is a high contrast ratio in the number of photons emitted between the solenoid "on" and "off" states. This contrast ratio is typically 1:100, although other ratios are contemplated.

The high atomic number material may be arranged in a spatial pattern. The pattern may be regular in nature, such as a square grid, with equally spaced high-z targets; or a triangular arrangement. An irregular pattern is also possible. Each high-z target may be a circle or ellipse. It may also be a square or rectangle. Another shape (e.g. an annular target) that may be of use is a crescent or other shapes formed from the intersection of circles, possibly two circles.

The term "not deflected and/or defocussed" may also be understood to mean "unaffected".

The ratio of the diameter of the high atomic number material to the distance between the adjacent high atomic number materials in the two dimensional pattern may be approximately 1:100.

The distance between adjacent areas of high atomic number materials may be approximately 1 cm.

Each individual target of the high atomic number material may be in the form of a circle having a diameter of approximately 100 µm.

The high atomic material in the target material may be tungsten, although other high atomic number materials are contemplated such as molybdenum, silver, gold and rhenium. The tungsten may have a thickness in the range 1 to 5 µm, although other thicknesses are contemplated such as 5 to 10 µm, 1 to 10 µm, greater than 10 µm, and less than 1 µm.

The low atomic material in the target material may be silicon, although other low atomic number materials or combinations of low atomic materials may be used such as carbon, graphite, carbon-graphite composites, beryllium alloys such as beryllium-copper, aluminium, and aluminium alloys. Non and low-conducting materials may be useful such as polymers, fibre-glass, glasses and ceramics. The silicon may have a thickness in the range 50 to 500 µm, although other thicknesses are contemplated such as 1 mm, and 100 µm to 5 mm.

The low atomic material effectively may act as an interstitial absorption region adjacent to the bremsstrahlung target. This interstitial absorption region is an area which may comprise one or more low atomic number materials which effectively do not produce high energy x-rays. The energy loss may still be through bremsstrahlung or other collisional energy loss, but the rate of energy gloss may be lower and hence the resulting x-ray photons may have less energy. These lower energy photons do not penetrate relatively far through the material. In this way, by diverting the electrons (either through deflection or defocusing or both), the x-ray production may be effectively turned off.

The geometry and size of the arrangement of the high atomic number material will depend upon the geometry of the field emitters and is chosen so that for a suitable current density in the windings of the coil, the defocusing and/or deflection cause 99% of the electrons to be deviated away from the path that they would have taken in the absence of a solenoid current and to impinge upon the high atomic number material. This figure of 99% was chosen such that the remaining electron population (1%) produces a background level below other common sources of noise and in-line with similar effects from other x-ray imaging modalities such as x-ray tube ramp up effects, scattering and peak-peak dose fluctuations, although other values may be used.

The ratio of the high atomic number material diameter to the distance between the adjacent high atomic number materials in the two dimensional pattern may be in the range between 1:50 and 1:200, however other ratios are possible providing the geometry is sufficient to contain the electron beam in the high atomic material (when the solenoid is energised) and in the low atomic material (when the solenoid is not energised).

The distance between adjacent areas of high atomic number materials may be approximately 1 cm, however other dimensions are contemplated such as approximately equal to the emitter pitch, approximately equal to the diameter of the target, 100 µm to 500 µm, 500 µm to 1 mm, 1 to 10 mm, and 10 to 30 mm.

Each individual target of the high atomic number material may be a circle of approximately 100 µm in diameter, although other shapes and dimensions are contemplated as discussed above.

One method of fabricating the high atomic number material geometry is by a combination of lithography and deposition. Due to the thicknesses involved, control of the deposition buffer gas partial pressure and/or use of a double lithographic pattern (big circles and small circles) are beneficial, as would be known to someone skilled in the art of microfabrication techniques.

The target material may comprise a thin sheet of x-ray absorbing material configured to absorb low energy x-ray photons produced by the action of electrons impinging upon the high atomic number material, the x-ray absorbing sheet being positioned at the rear surface of the substrate containing target material.

The x-ray absorbing sheet may be positioned behind the target material and used for absorbing low energy x-ray photons produced by the action of electrons impinging upon the high atomic number material. This layer may allow for "hardening" or "stiffening" of the spectrum by absorbing the very low energy x-rays which do not contribute to the image formation but do otherwise increase the dose to the patient or target. It is also possible to incorporate this "hardening" layer into the low atomic material region.

The thin sheet of x-ray absorbing material may comprise aluminium of thickness in the range 0.1 to 1 cm, although other materials and thicknesses are also contemplated such as copper, aluminium-copper composites and alloys.

The plurality of energisable solenoid coils may comprise copper coils, fabricated by electroforming windings of small sheets of copper.

Other materials and methods of fabrication may also be used such as wound coils comprising aluminium wire, rolled coils from conducting sheets separated by insulating sheets (such as Mylar®), a single turn made from thick conductors may also be used, as well as so-called 'Tesla spirals' of flat coils.

The solenoid coils may be wired with rectangular sheets of copper of high packing factor, the sheets may be 5 microns by 10 microns, although other sheet sizes are useful.

In one embodiment the length of the solenoid will be covered with 100 turns and the thickness will be made up of 10 layers each of which has 10 turns although other arrangements are useful. The layers can be wired in series which is more common in solenoid optimisation. In an embodiment the layers will be wired in parallel for faster response and higher current/lower voltage supplies.

In one embodiment thirty six solenoid coils are arranged in a two dimensional 6×6 arrangement. This embodiment has the advantage that with a 1 cm pitch between the solenoids it is possible to fabricate all thirty six coils on a 4" (100 mm) wafer as widely used within electronics semiconductor processing. Other embodiments containing sixty four coils arranged in an 8×8 grid or forty nine coils arranged in a 7×7 grid are also useful.

The array may be considered to be a tile. The number of coils may depend on the total size and hence total number of emitters. For instance, for a 42×42 cm general radiology panel source, there may be approximately 1764 emitters. Alternatively, there may be a 40×40cm source with 1600 emitters. This may require up to 1680 or more coils.

Power may be is supplied to the thirty six solenoid coils through thirty six power control lines. This may be achieved through the use of two 1×32 multiplexer devices (MUXs) which act as a large switching array under the control of a microprocessor or microcontroller. Other switching mechanisms and devices would be known to those skilled in electronic power switching and would serve the same purpose of being able to provide power independently to each solenoid to achieve a desired scanning sequence according to the imaging modality being undertaken.

It will be appreciated that there are several design approaches for implementing a suitable array of magnetic field generators such that the emitted electrons may be deflected or defocused. It may be further appreciated that electrostatic approaches may be used, but with the added challenge of introducing conductors between the cathode and anode (target) region which would make the design prone to breakdown. Therefore, in one embodiment magnetic fields, produced with coils and shaped by ferric lenses, are employed.

In one embodiment the electron emitters will be formed by a pyroelectric crystal with an upper surface and a conducting film coating the upper surface of the pyroelectric crystal. The pyroelectric crystal includes a plurality of field emitters formed as micrometer-scale exposed regions in the pyroelectric crystal having one or more sharp peaks or ridges. The pyroelectric crystal is alternately heated and cooled over a period of several minutes with a heater/cooler adjacent the pyroelectric crystal so that spontaneous charge polarisation occurs in the pyroelectric crystal. The spontaneous charge polarisation causes a perpendicular electric field to arise on the pyroelectric crystal's top and bottom faces, in which case at the exposed surface of the pyroelectric crystal the electric field is enhanced by the sharp peaks or ridges, thereby causing field emission of surface electrons from that location. X-rays are produced when the emitted electrons strike a target material located adjacent to the emitting face.

The pyroelectric crystal may comprise or consist of lithium niobate.

In an alternative embodiment, the electron emitter may be a non-pyroelectric source.

The electron emitter may be field enhanced emitter, a cold cathode, a thermionic cathode or a photocathode.

A plurality of magnetic lenses may be positioned adjacent to the plurality of energisable solenoid coils, the magnetic lenses being arranged such that in use, the lens may concentrate the field flux towards the centre of the emitter array.

The electronic power and timing circuit may be configured such that in use it provides current to individual solenoids in a raster sequence.

The x-ray generator may be configured such that adjacent solenoid coils are energisable within 1 ms to 5 ms of each other.

In this regard, the electronic power and timing circuit may be configured to provide current to a number of solenoid coils simultaneously.

The x-ray generator may further comprise an input control device configured to provide current to a number of solenoid coils simultaneously based on a selection of a region of interest.

In this regard, the x-ray technician may select the region of interest or software may automatically select it. Then, the corresponding emitters which at least cover that region of interest may be activated while the emitters which are either not at all, or by only a small amount, within the region of interest are left switched-off (inactive). The control software may determine which emitters are part of the region of interest.

Alternatively, the operator may manually select a fraction of the panel to activate. For instance, the operator may elect to only use the left side or the upper right quarter of the panel. The remaining portions of the panel would then remain inactive.

The software may choose to activate only every other emitter, for instance, as may be used in a quick, lower resolution "scout" scan.

Regarding the use of multiple emitters simultaneously this is a matter of, in general, speeding up the total raster while still preventing overlaps (in a single frame). The raster may be multiplexed by dividing the panel into regions where emission from two emitters on opposite corners of regions would not overlap if activated. Each region may operate in parallel. If four regions are calculated to not overlap, then four coils may be activated simultaneously and each coil incremented.

The electronic power and timing circuit may be configured to provide current to a number of solenoid coils simultaneously as synchronised by an external clock signal.

Each electron emitter may comprise a pyroelectric crystal arranged to emit electrons when thermally cycled.

The invention claimed is:

1. A method of generating x-rays comprising the steps of:
emitting a plurality of electron beams from a plurality of electron beam emitters arranged in an array;
energizing a subset of a plurality of solenoid coils arranged in an array and disposed adjacent to the plurality of electron beam emitters, wherein each of the energized solenoid coils generates a magnetic field;
deflecting a subset of the plurality of electron beams to strike at least one target, thereby generating x-ray photons;
detecting the x-ray photons at a detector after the x-ray photons pass through a region of interest; and
generating an image of at least a portion of the region of interest using information provided by the detector.

2. The method of generating x-rays of claim 1, wherein the subset of the plurality of solenoid coils is selected based on the region of interest.

3. The method of generating x-rays of claim 1, wherein the subset of the plurality of solenoid coils are energized in a raster sequence.

4. The method of generating x-rays of claim 1, wherein the generated image comprises an image of at least a portion of an object located within the region of interest.

5. An x-ray generator, comprising:
a plurality of electron field emitters arranged in an array, wherein each of the electron field emitters is capable of emitting one of a plurality of electron beams;
a plurality of targets disposed adjacent to the electron field emitters and capable of emitting x-ray photons when struck by one of the plurality of electron beams;
a plurality of solenoid coils arranged in an array and disposed adjacent to the plurality of electron field emitters; and
a circuit capable of individually energizing each of the plurality of solenoid coils
to thereby generate a magnetic field which deflects a respective one of the plurality of electron beams.

6. The x-ray generator of claim 5, wherein the circuit energizes each of the plurality of solenoid coils in a raster sequence.

7. The x-ray generator of claim 5, wherein the circuit is capable of energizing adjacent ones of the plurality of solenoid coils within 1 ms to 5 ms of each other.

8. The x-ray generator of claim 5, wherein the circuit is capable of determining which of the plurality of solenoid coils to energize based on a region of interest.

9. The x-ray generator of claim 5, wherein the target material is distributed in a circle having a diameter of approximately 100 μm.

10. The x-ray generator of claim 5, wherein the target material is disposed within a low atomic material.

11. The x-ray generator of claim 10, further comprising a thin sheet of x-ray absorbing material capable of absorbing low energy x-ray photons, wherein the thin sheet of x-ray absorbing material is positioned at a rear surface of the low atomic material.

12. The x-ray generator of claim 5, wherein the first solenoid coil comprises copper coils fabricated by electroforming windings of small sheets of copper.

13. The x-ray generator of claim 5, wherein the circuit is capable of separately providing the electrical current to each of the plurality of solenoid coils within 1 ms to 5 ms of each other.

14. The x-ray generator of claim 5, wherein the circuit is capable of providing the electrical current to the plurality of solenoid coils simultaneously.

15. The x-ray generator of claim 5, wherein the circuit provides the electrical current to a subset of the plurality of solenoid coils in response to an external clock signal.

16. The x-ray generator of claim 5, wherein the circuit provides the electrical current to a subset of the plurality of solenoid coils based on whether the subset of solenoid coils is within a region of interest.

17. The x-ray generator of claim 5, wherein the plurality of electron emitters each comprise a pyroelectric crystal arranged to emit electrons when thermally cycled.

18. The x-ray generator of claim 5, wherein the magnetic field deflects the beam of electrons such that the beam of electrons strikes the target material and the target material emits the x-ray photons.

19. The x-ray generator of claim 5, wherein the magnetic field deflects the beam of electrons such that the beam of electrons stops striking the target material and the target material stops emitting the x-ray photons.

20. A method of generating x-rays comprising the steps of:
    emitting a plurality of electron beams from a plurality of electron beam emitters arranged in an array;
    de-energizing a subset of a plurality of solenoid coils arranged in an array and disposed adjacent to the plurality of electron beam emitters, wherein each of the energized solenoid coils then ceases to generate a magnetic field;
    so that a subset of the plurality of electron beams strikes at least one target, thereby generating x-ray photons;
    detecting the x-ray photons at a detector after the x-ray photons pass through a region of interest; and
    generating an image of at least a portion of the region of interest using information provided by the detector.

21. The method of generating x-rays of claim 20, wherein the subset of the plurality of solenoid coils is selected based on the region of interest.

22. The method of generating x-rays of claim 20, wherein the subset of the plurality of solenoid coils are energized in a raster sequence.

23. The method of generating x-rays of claim 20, wherein the generated image comprises an image of at least a portion of an object located within the region of interest.

* * * * *